(12) United States Patent
Hwang et al.

(10) Patent No.: US 7,327,464 B2
(45) Date of Patent: Feb. 5, 2008

(54) SYSTEM AND METHOD FOR COHERENT OPTICAL INSPECTION

(75) Inventors: Shiow-Hwei Hwang, Livermore, CA (US); Tao-Yi Fu, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/738,756

(22) Filed: Apr. 23, 2007

(65) Prior Publication Data

US 2007/0195332 A1 Aug. 23, 2007

Related U.S. Application Data

(62) Division of application No. 10/678,920, filed on Oct. 2, 2003, now Pat. No. 7,209,239.

(60) Provisional application No. 60/415,791, filed on Oct. 2, 2002.

(51) Int. Cl.
*G01B 9/02* (2006.01)
*G01B 11/02* (2006.01)
(52) U.S. Cl. ..................... 356/495; 356/511
(58) Field of Classification Search ................ 356/491, 356/492, 495, 511, 512, 513, 514, 516
See application file for complete search history.

(56) References Cited

U.S. PATENT DOCUMENTS

| | | | |
|---|---|---|---|
| 3,635,552 A * | 1/1972 | de Lang | ..................... 356/495 |
| 4,340,304 A | 7/1982 | Massie | |
| 5,129,724 A | 7/1992 | Brophy et al. | |
| 5,293,538 A | 3/1994 | Iwata et al. | |
| 5,666,197 A | 9/1997 | Guerra | |
| 5,764,363 A * | 6/1998 | Ooki et al. | ................. 356/364 |
| 5,914,782 A * | 6/1999 | Sugiyama | .................... 356/491 |
| 5,999,261 A | 12/1999 | Pressesky et al. | |
| 6,034,814 A * | 3/2000 | Otaki | .......................... 359/371 |
| 6,078,392 A | 6/2000 | Thomas et al. | |
| 6,122,046 A | 9/2000 | Almogy | |
| 6,262,818 B1 | 7/2001 | Cuche et al. | |
| 6,943,898 B2 | 9/2005 | Libinson et al. | |
| 2003/0227618 A1 | 12/2003 | Some | |

OTHER PUBLICATIONS

C. Koliopoulos, "Simultaneous Phase Shift Interferometer," *Advanced Optical Manufacturing and Testing II*, Proc. SPIE vol. 1531, pp. 119-127 (1991).
USPTO, "Office Action," mailed in related U.S. Appl. No. 10/678,920 on Dec. 13, 2005, 15 pages.
USPTO, "Office Action," mailed in related U.S. Appl. No. 10/678,920 on Jun. 22, 2006, 9 pages.

* cited by examiner

*Primary Examiner*—Michael A. Lyons
(74) *Attorney, Agent, or Firm*—Davis Wright Tremaine LLP

(57) ABSTRACT

A system and method for coherent optical inspection are described. In one embodiment, an illuminating beam illuminates a sample, such as a semiconductor wafer, to generate a reflected beam. A reference beam then interferes with the reflected beam to generate an interference pattern at a detector, which records the interference pattern. The interference pattern may then be compared with a comparison image to determine differences between the interference pattern and the comparison image. According to another aspect, the phase difference between the reference beam and the reflected beam may be adjusted to enhance signal contrast. Another embodiment provides for using differential interference techniques to suppress a regular pattern in the sample.

16 Claims, 11 Drawing Sheets

FIG. 6A
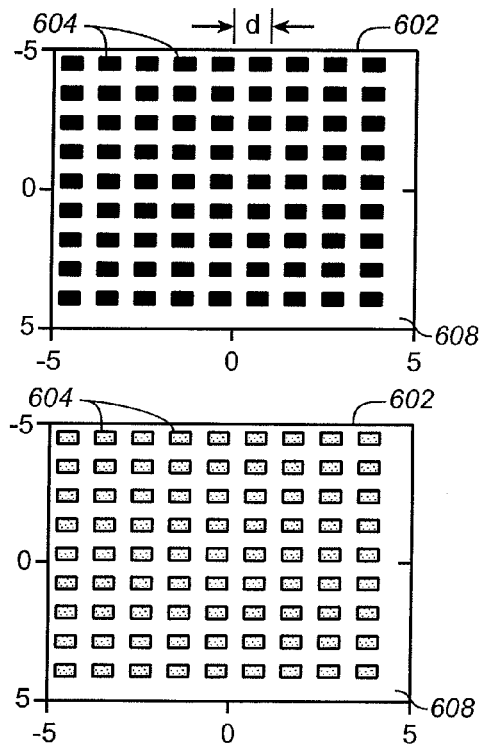
FIG. 6B
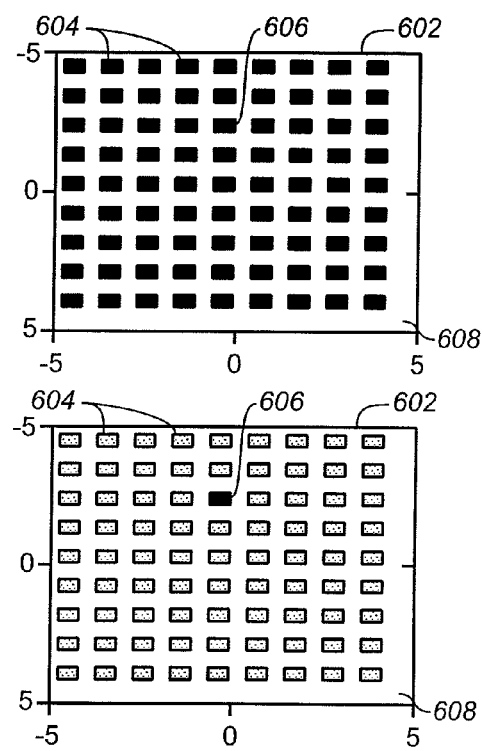
FIG. 6C
FIG. 6D
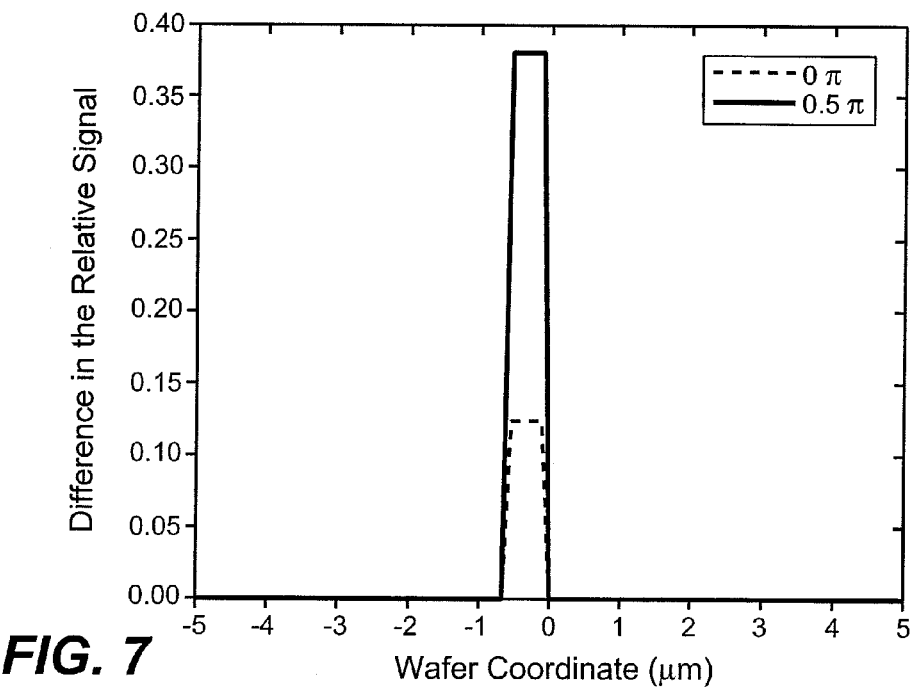
FIG. 7

SYSTEM AND METHOD FOR COHERENT OPTICAL INSPECTION

This application is a divisional of U.S. Non-Provisional Patent Application No. 10/678,920, filed on Oct. 2, 2003, now U.S. Pat. No. 7,209,239, which claims the benefit of U.S. Provisional Patent Application No. 60/415,791, filed on Oct. 2, 2002, which applications are incorporated by reference herein in their entirety.

TECHNICAL FIELD

The present system and method generally relate to the inspection of surfaces to detect defects, and in particular, to an improved system and method that is useful in detecting defects using coherent optical inspection techniques.

BACKGROUND

Conventionally, defect detection on semiconductor wafers can be done with either optical or electron beam inspection. Systems and methods for inspecting semiconductor wafers for defects using optical and electron beam inspection techniques are well known.

Optical inspection systems frequently use either microscopic type imaging and/or the collection of the scattered energy. For the microscopic type of optical inspection, it may be difficult to inspect defects that generate little intensity change from the nominal structures. For example, dark defects on a dark background are typically difficult to detect due to the closeness of the change in intensity in the reflected image due to the dark defect on the dark background.

It has been found that, in some applications, defect detection can be improved by using phase detection rather than intensity based detection, because defects that create little intensity or little intensity change typically would have a modest phase signal.

One system for defect detection using phase detection is disclosed in U.S. Pat. No. 6,078,392, which is incorporated herein by reference in its entirety. This patent proposes a direct-to-digital holography approach wherein a collimated reference beam is incident upon a reference beam mirror at a non-normal angle, and the reference beam and an object beam that is focused at a focal plane of a digital recorder to form an image. This direct-to-digital holography approach, however, requires significant computational power, which may limit throughput. Further, this approach may be cumbersome by requiring the reference beam to be incident upon a reference beam mirror at a non-normal angle.

Another patent that refers to use of digital holograms is U.S. Pat. No. 6,262,818, the disclosure of which is incorporated herein by reference in its entirety. This patent refers to a method for simultaneous amplitude and quantitative phase contrast imaging by numerical reconstruction of digital holograms. This approach also requires significant computational power, which may limit throughput.

SUMMARY

In general, the present system and method provide for enhanced defect signal contrast for microscopic optical inspection of a sample, such as a semiconductor wafer, by using coherent optical detection techniques.

One embodiment of the present invention employs coherent optical detection such that the output is proportional to the amplitude of the light reflected from the sample rather than the intensity of the light reflected from the sample. In general, an interference pattern between a complex field reflected from the sample and common reference beam is detected and recorded. This interference pattern is then compared with a comparison image to determine differences between the interference pattern and the comparison image.

Specifically, one implementation of this embodiment provides for inspecting a sample by illuminating at least a portion of a sample with an illumination beam to generate a reflected beam and interfering a first reference beam and the reflected beam to generate an interference pattern. This interference pattern is then recorded and compared with a comparison image to detect differences between the recorded interference pattern and the comparison image. The comparison between the recorded interference pattern and the comparison image may comprise taking the difference of the recorded interference pattern and the comparison image to generate a difference field or value.

Another embodiment of the present invention utilizes interference contrast enhancement to boost a defect signal and improve contrast of the recorded interference pattern. The amplitude of the reference beam may be adjusted to boost the signal for certain areas of the sample being inspected. Also, the phase difference between the reference beam and the complex field may be adjusted to enhance contrast.

Specifically, one implementation of this embodiment provides for inspecting a sample by illuminating at least a portion of a sample with an illumination beam to generate a reflected beam and interfering a first reference beam and the reflected beam to generate a first interference pattern. The first interference pattern is then recorded. The phase of the illumination beam is then adjusted to enhance contrast between a first portion of the first interference pattern and a second portion of the first interference pattern.

Another implementation of this embodiment includes interfering a second reference beam and the reflected beam to generate a second interference pattern at a second detector with the second reference beam having a different phase than the first reference beam. The phase difference between the first and second reference beams may be ninety degrees. In this implementation, adjusting the phase of the reference beam further includes adjusting the phase of the reference beam based on at least portions of the first and second interference patterns.

Another embodiment of the present system and method utilize interference, such as differential interference, to suppress regular patterns in a sample to enhance a defect signal. Specifically, according to one implementation of this embodiment, a sample having an array of regularly spaced features may be inspected by illuminating the sample with an illumination beam to generate a reflected beam and laterally separating the reflected beam into first and second beams. The regularly spaced features of the sample are positioned a distance d from each other. The first and second beams are displaced from one another by a displacement distance equal to a multiple of the distance d, the second beam being about 180 degrees out of phase with the first beam. The first beam and the second beam interfere with each other to generate an interference pattern, which is detected. By subtracting a pattern that is laterally shifted from the pattern of a sample, the effect of the pattern is suppressed. The interference can be performed, for example, by using division by wavefront techniques, such as Fourier filtering, or division by amplitude, such as shearing through polarization or beam-splitting. The interference may be optionally performed using a Nomarski layout.

Other important technical details and advantages of the present invention are readily apparent to one skilled in the art from the following figures, descriptions, and claims.

BRIEF DESCRIPTION OF THE DRAWINGS

For a more complete understanding of the present invention and for further features and advantages, reference is now made to the following description taken in conjunction with the accompanying drawings, in which:

FIGS. 6A, 6B, 6C, and 6D illustrate a simulated signal plot of array patterns obtained using coherent detection methods.

FIG. 7 is a plot of a difference signal across an area surrounding a feature of the FIG. 6D plot with the phase of the reference beam set at 0.0 and with the phase of the reference beam set at π/2.

DETAILED DESCRIPTION

Figure 1:
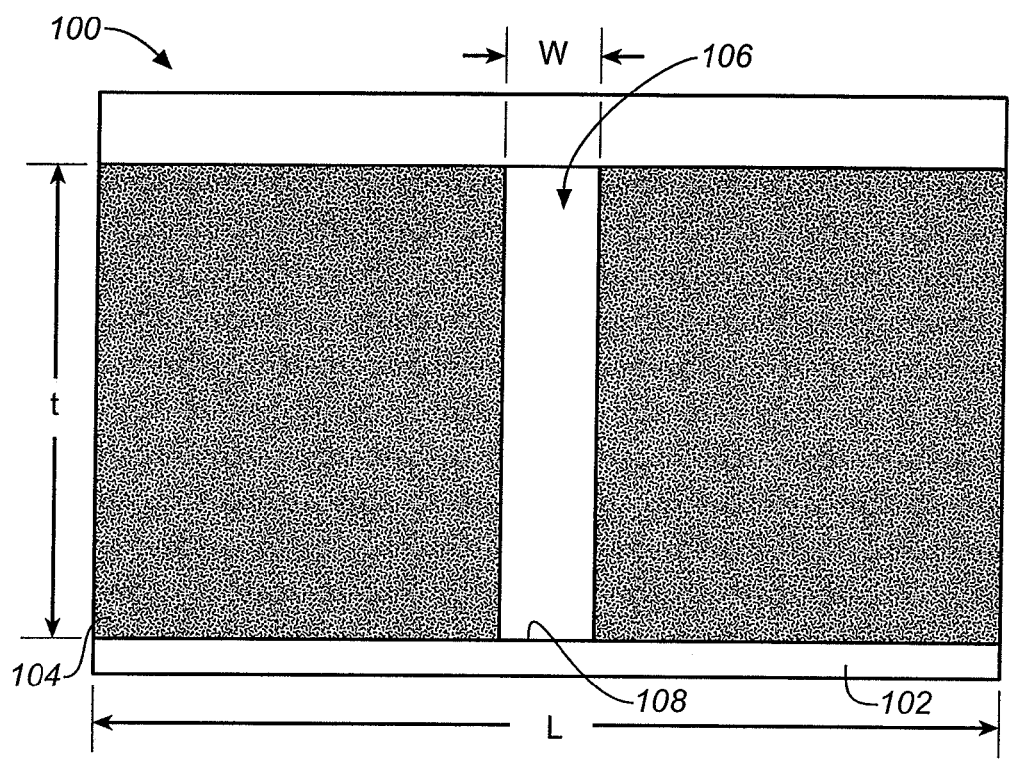
FIG. 1 illustrates a portion of a sample to be inspected.

FIG. 1 is a cross-sectional view of one embodiment of portion of a sample 100. As shown, the sample 100 includes a metal layer 102 having a length L and a $SiO_2$ layer 104 having a thickness t disposed on the metal layer 102. A hole 106 having a width w is formed in the $SiO_2$ layer 104 and may comprise a via or trench, for example. The hole 106 extends the entire thickness of the $SiO_2$ layer 104 and exposes a portion 108 of the metal layer 102. In an example embodiment, the $SiO_2$ layer 104 may have a thickness t of about 1400 nanometers and the hole 106 may have a width w of about 300 nanometers and the metal layer 102 may have a length L. In this configuration, the hole 106 may be considered a "high aspect ratio" or (HAR) structure, due to the magnitude of the ratio of the depth of the hole 106 to the width of the aperture 106. In this example, the aspect ratio is 1400/300, or about 4.67. HAR structures may have aspect ratios in the range of about 1:1 to about 12:1, and in some cases 4:1 to about 12:1.

As a result of certain manufacturing processes, film residue (not shown), or other non-conductive matter, were left in the aperture 106 and deposited on the exposed portion 108 of the metal layer 102, thereby limiting or preventing electrical connection to the exposed portion 108 of the metal layer 102 through the aperture 106. This film residue deposited on the exposed portion 108 of the metal layer 102 may comprise a defect or anomaly in the sample. Accordingly, it is desirable in some applications to be able to detect the presence of the film residue.

Figure 2A:
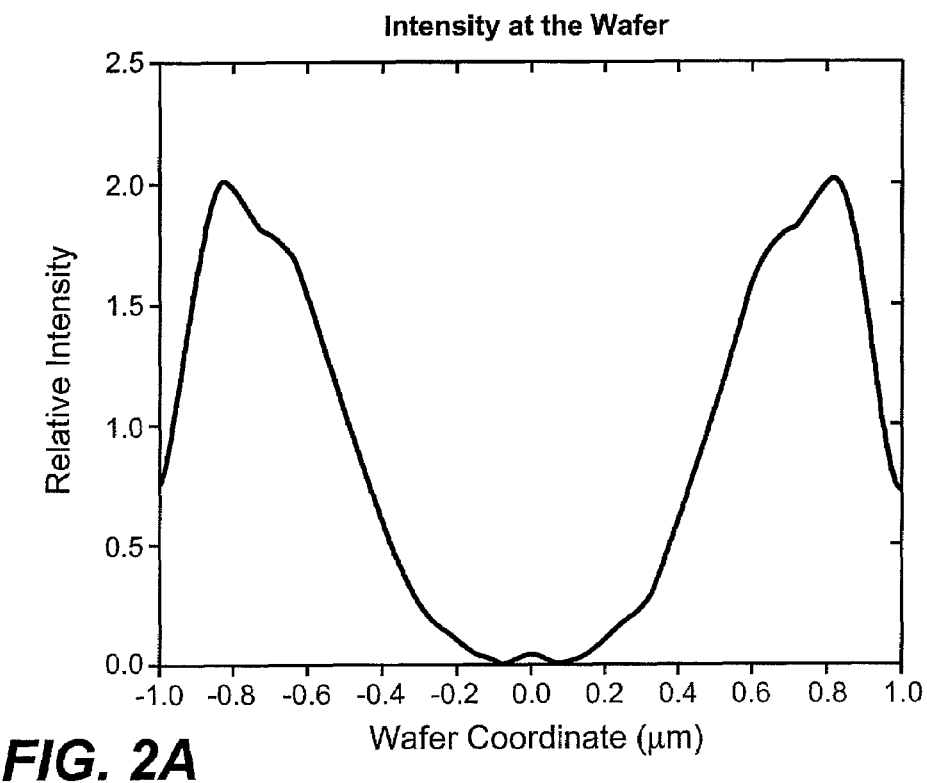
FIGS. 2A and 2B illustrate signal plots detected from the sample of FIG. 1.
Figure 2B:
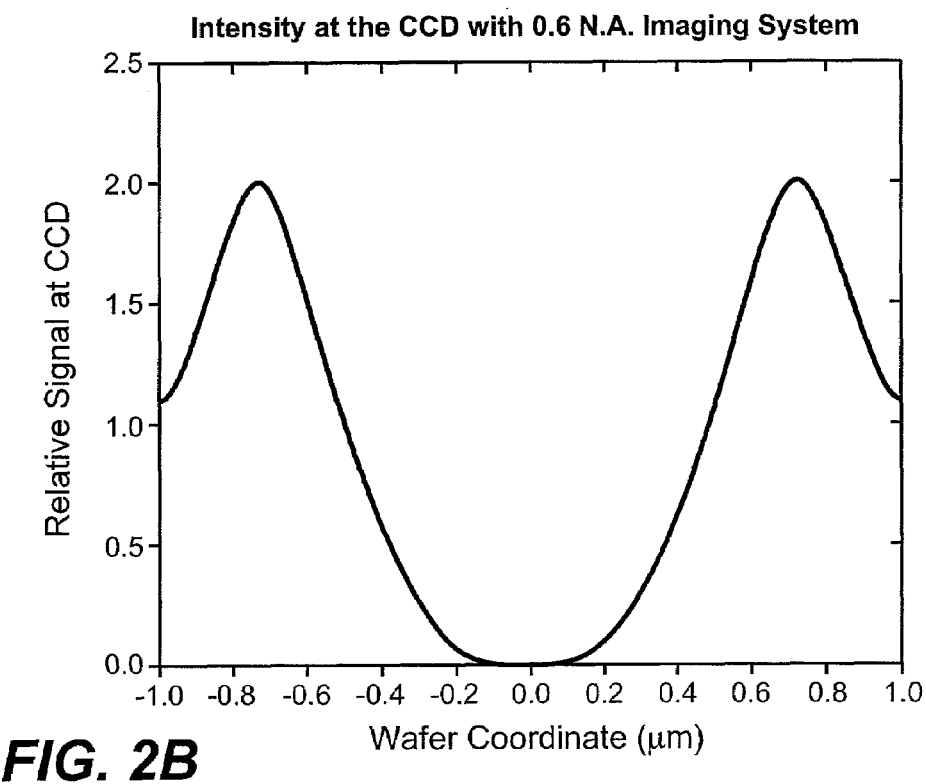

When an illuminating beam illuminates the sample 100, the area including the aperture 106 generates significantly lower intensity from the exposed portion 108. FIGS. 2A and 2B are plots of the simulated signal as may be seen on a charge coupled device (CCD) camera for conventional intensity-based microscopic detection. In particular, FIG. 2A is a plot of the relative intensity at the sample 100 and FIG. 2B is a plot of the intensity at the CCD camera with a 0.6 numerical aperture imaging system. FIGS. 2A and 2B generally illustrate that relatively little intensity is being detected from the exposed area 108 of the metal layer 102 and that the signal detected from the exposed area 108 will be greatly affected by the noise in the electronics and the detector noise.

Coherent Detection

Figure 3A:
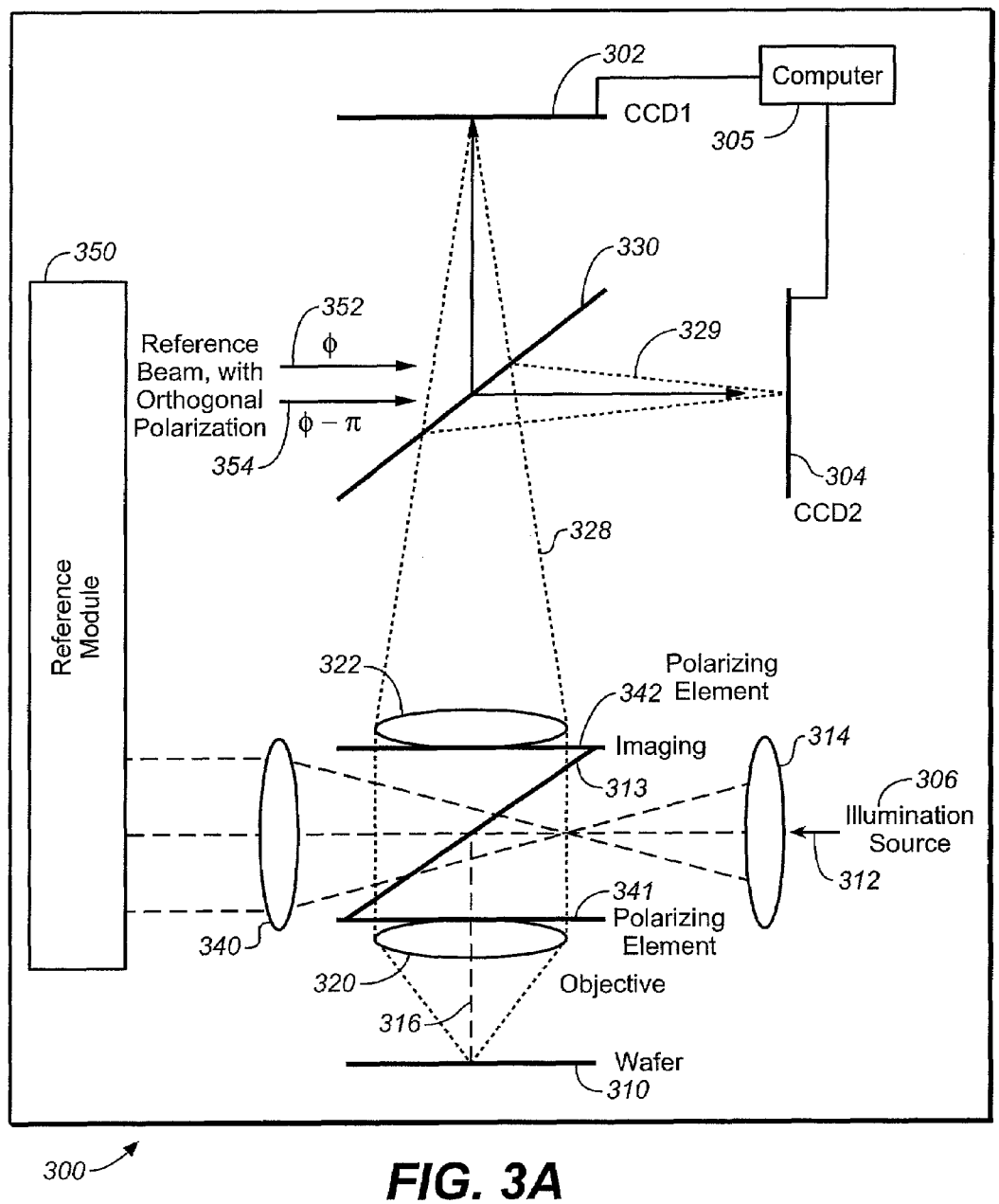
FIG. 3A schematically illustrates an example imaging system in accordance with an embodiment of the present invention.

FIG. 3A is a schematic view of an example inspection and imaging system 300 according to one embodiment of the present invention. The system 300 is configured for inspecting a sample 310, which may comprise a semiconductor wafer or other suitable object to be inspected. As illustrated, the system 300 generally includes detectors 302, 304, an illumination source 306, and a sample 310, such as a semiconductor wafer. The detectors 302, 304 may comprise CCD cameras or other suitable image capture devices. The detectors 302, 304 are connected to a computer 305 or other data processing device, for storing detected images and performing analysis of the same. The illumination source 306 outputs an illumination beam 312, which is transmitted through lens 314. In some embodiments, the illuminating source may comprise a laser beam generator or other narrow band light source and the illuminating beam may comprise laser light.

The illuminating beam 312 travels to a beam splitter 313. The beam splitter 313 may be, for example, 50% reflective. Light that is reflected from the beam splitter 313 constitutes an object beam 316 and travels toward the sample 310 via an objective lens 320, which collimates the light to illuminate the sample 310 with a collimated beam. A portion of the light reflected from the sample 310 comprises a reflected beam 328 and passes through the beam splitter 313 and an imaging lens 322 for detection by one or more detectors 302, 304. As illustrated in FIG. 3A, a component of the reflected beam 328 travels to the detector 302 by passing through a beam splitter 330. Another component 329 of the reflected beam 328 travels to the detector 304 by reflecting from the beam splitter 330. The beam splitter 330 may be, for example, 50% reflective. Alternatively, the beam splitter 330 may comprise a polarizing beam splitter.

In an alternate embodiment (not illustrated), the detector 304 is not present and the reflected beam 328 travels to the detector 302 for detection.

Figure 3B:
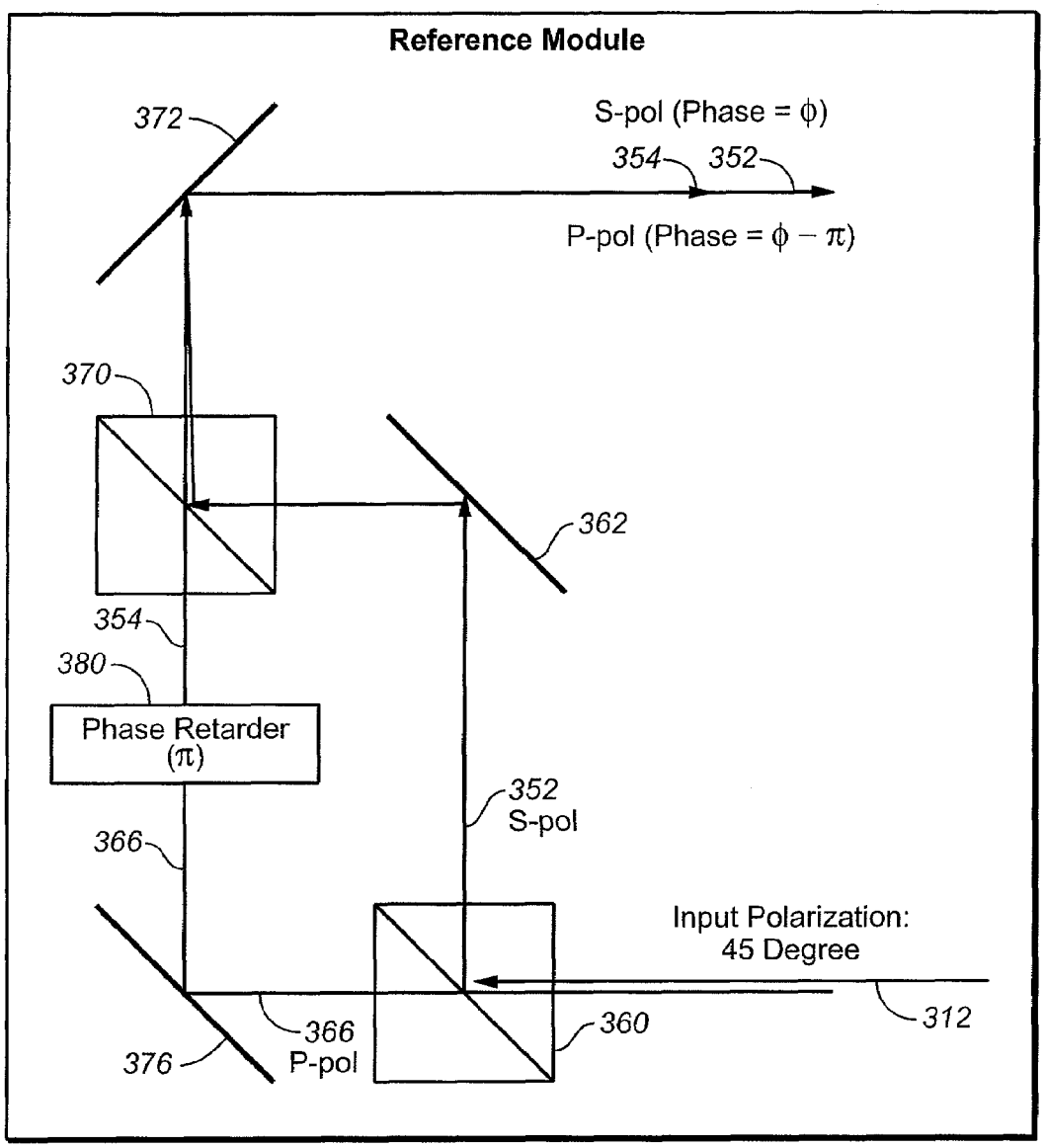
FIG. 3B schematically illustrates details of an example embodiment of the FIG. 3A reference module.

A component of the collimated illumination beam 312 passes through the beam splitter 313 and travels through a lens 340 to a reference module 350. Details of one example reference module 350 are illustrated in FIG. 3B and are described below. In one embodiment, the component of the illumination beam 312 that passes through the beam splitter 313 has a polarization of about 45 degrees with respect to an axis of polarizing beam splitter 360.

The reference module 350, as described in more detail below with reference to FIG. 3B, outputs a first reference beam 352 having phase $\Phi$ and a second reference beam 354 having phase $\Phi$-$\pi$. Hence, the first and second reference beams 352, 354 are out of phase by 180 degrees. The first and second reference beams 352, 354 can alternatively be out of phase by 90 degrees. Further, the first and second reference beams 352, 354 are polarized orthogonal to each other.

The first and second reference beams 352, 354 are substantially collinear and travel to the beam splitter 330. The beam splitter 330 transmits light having a first polarization and reflects light having a polarization orthogonal to the first polarization. Since the first and second reference beams 352, 354 are polarized orthogonal to each other, the beam splitter 330 reflects one of first and second reference beams 352, 354 towards the detector 302 and transmits the other of the first and second reference beams 352, 354 to the detector 304. In one embodiment, the first reference beam 352 reflects from the beam splitter 330 towards the detector 302.

Accordingly, at least a portion of the reflected beam 328 and the first reference beam 352 interfere with each other at the detector 302 and generate a first interference pattern, which is detected by the detector 302. The first interference pattern results from the interference of the first reference beam 352 and at least a portion of the reflected beam 328.

Likewise, at least a portion of the reflected beam 329 and the second reference beam 354 interfere with each other at the detector 304 and generate a second interference pattern, which is detected by the detector 304. The second interference pattern results from the interference of the second reference beam 354 and at least a portion of the reflected beam 329.

In operation, the first interference pattern, as detected by the detector 302, is compared with a comparison image to detect, or determine, differences between the first interference pattern and the comparison image.

For example, the comparison image may comprise an interference pattern obtained from a comparison sample (not shown). The comparison sample is positioned at the location of sample 310 in FIG. 3A. Next, the comparison sample is illuminated using the illumination beam 312 to generate a reflected beam 328 as described above. At least a portion of this reflected beam 328 is then interfered with the first reference beam 352 to generate a comparison interference pattern at the detector 302. The detector 302 detects and records the comparison interference pattern. This comparison interference pattern is then stored at the computer 305 for later comparison with the first interference pattern.

The first interference pattern is compared with the comparison image to detect differences between the first interference pattern and the comparison image. Significant differences between the first interference pattern and the comparison image may be associated with significant differences in the physical structures of the comparison sample and the sample 310. These differences in the physical structures of the comparison sample and the sample 310 may comprise defects.

In one embodiment, computer 305 compares the first interference pattern with the comparison image by subtracting the first interference pattern from the comparison image to determine or detect the differences between the first interference pattern and the comparison image. In another embodiment, computer 305 compares the first interference pattern with the comparison image by subtracting the comparison image from the first interference image to determine or detect the differences between the first interference pattern and the comparison image.

In general, the detector 302 detects the intensity of the first interference pattern. The intensity of the first interference pattern may be expressed as follows, where $I_{det(A)}$ is the intensity of the first interference pattern at the detector 302, $E_{(A)}$ is the amplitude of the reflected beam 328, $E_{ref(1)}$ is the amplitude of the first reference beam 352, $\Phi_{(A)}$ is the phase of the reflected beam 328 and $\Phi_{ref(1)}$ is the phase of the first reference beam 352.

$$I_{det(A)} = |E_{(A)} e^{i\,\Phi(A)} + E_{ref(1)} e^{i\,\Phi ref(1)}|^2 \quad (1)$$

$$I_{det(A)} = |E_{(A)}|^2 + |E_{ref(1)}|^2 + 2|E_{(A)} \times E_{ref(1)}{}^*| \times \cos(\Phi_{(A)} - \Phi_{ref(1)}) \quad (2)$$

Assuming that the amplitude squared of the beam reflected from the comparison image ($E_{(B)}{}^2$) equals the $E_{(A)}{}^2$ and assuming $E_{ref(1)}$ to be constant, subtracting the intensity $I_{det(B)}$ associated with the comparison image from the $I_{det(A)}$ associated with the sample 310 yields the following.

$$I_{det(A)} - I_{det(B)} = 2E_{(A)}E_{ref(1)} \cos(\Phi_{(A)} + \Phi_{ref(1)}) - 2E_{(B)}E_{ref(1)} \cos(\Phi_{(B)} + \Phi_{ref(1)}) \quad (3)$$

Accordingly, the difference $I_{det(A)} - I_{det(B)}$ between the first interference pattern $I_{det(A)}$ and the comparison image $I_{det(B)}$ is heavily dependent on $\cos(\Phi_{(A)} + \Phi_{ref(1)}) - \cos(\Phi_{(B)} + \Phi_{ref(1)})$, or the difference in phase change between the first interference pattern and the comparison image. When the difference $I_{det(A)} - I_{det(B)}$ between the first interference pattern $I_{det(A)}$ and the comparison image $I_{det(B)}$ exceeds a predetermined maximum threshold, it may be concluded that a significant structural difference exists between the sample 310 and the comparison sample. The difference $I_{det(A)} - I_{det(B)}$ between the first interference pattern $I_{det(A)}$ and the comparison image $I_{det(B)}$ may be referred to as the "defect signal."

Further, it should be noted that by increasing the amplitude of the first reference beam $A_{ref(1)}$, the magnitude of the defect signal may be boosted. Moreover, adjusting the phase of the reference beam may further increase the defect signal. In one embodiment, the phase of the reference beam is adjusted to provide optimal contrast between a defect and a background pattern associated with the defect. As explained below, providing optimal contrast can mean providing maximum or minimum contrast between a defect and a background pattern associated with the defect. In another embodiment, the phase of the reference beam is adjusted to provide contrast between a nominal structure and a corresponding defect structure.

FIG. 3B illustrates details of an example embodiment of the reference module 350 of FIG. 3A. As illustrated, the reference module 350 receives as input a component of the illumination beam 312 and outputs the first and second reference beams 352, 354. In one embodiment, the component of the illumination beam 312 received by the reference module 350 has a 45 degree polarization relative to a polarizing cube beam splitter 360. In one embodiment, the illumination path to the sample includes a polarizing element (341) to control the polarization incident to the sample and another polarizing element (342) to rotate the polarization of the return beam so it has equal intensity for the S and P polarization component.

The polarizing cube beam splitter 360 may be constructed of two cemented right angle prisms. As illustrated, P-polarized light is transmitted, and S-polarized light is reflected 90°. Outside surfaces may have an anti-reflection coating to reduce back reflections. Typically, no beam displacement occurs between the original and separated beams. The reflected and transmitted beams travel through about the same amount of glass, so although the optical path length of each arm is increased, both paths are increased by the same amount. The cubic shape of the cube beam splitter 360 makes the cube beam splitter easy to mount in some applications, thus suffering less from deformation due to mechanical stress. The cube beam splitter 360 is polarization sensitive and outputs an s-polarization component S-pol and a P-polarization components P-pol. The S-Polarized component of the illuminating beam 312 comprises the first reference beam 352 and the P-Polarized component of the illuminating beam 312 comprises an intermediate beam 366.

The S-Polarized component of the illuminating beam 312, which comprises the first reference beam 352 is reflected by the cube beam splitter 360 and travels from the polarizing cube beam splitter 360 at 90° from the angle at which the illuminating beam 312 enters the cube beam splitter 360. The first reference beam 352 then travels to mirror 362 and reflects from the mirror 362 at 90° toward cube beam splitter 370. The first reference beam 352 then enters a cube beam splitter 370 and exits the cube beam splitter 370 at 90° relative to the angle at which the first reference beam 352 enters the cube beam splitter 370. Because the first reference beam 352 is S-polarized, the first reference beam is reflected by the cube beam splitter 370. The first reference beam 352 exits the cube beam splitter 370 and travels toward a mirror 372 and reflects from the mirror 372 at 90° relative to the angle at which the first reference beam 352 is incident at the mirror 372 and exits the reference module 350 toward the beam splitter 330 (FIG. 3A).

The intermediate beam 366 exits the cube beam splitter 360 and travels toward a mirror 376. The intermediate beam 366 reflects from the mirror 376 at 90° relative to the angle at which the intermediate beam 366 is incident at the mirror 376 towards a phase retarder 380. The phase retarder 380 may comprise a conventional phase retarder that receives the intermediate beam 366, retards the phase of the intermediate beam 366 by $\pi$, and outputs the second reference beam 354, the second reference beam 354 lagging the intermediate beam 366 by $\pi$. Thus, where the optical path lengths between beam splitters 360 and 370 are substantially the same for beams 352 and 354, the second reference beam 354 will have a phase difference of $\pi$ relative to the first reference beam 352. Phase retarders that cause a phase difference other than $\pi$ may alternatively be employed. In one embodiment, the phase retarder causes a phase difference of $n*2\pi\pm\pi$, where n is an integer, although other phase differences may also be employed. The second reference beam 354 exits the phase retarder 380 and travels towards the mirror 372, passing through the cube beam splitter 370. The second reference beam 354 then reflects from the mirror 372 at 90° relative to the angle at which the second reference beam 354 is incident at the mirror 372. The second reference beam 354 exits the reference module 350 toward the beam splitter 330 (FIG. 3A). As shown in FIG. 3B, the first and second reference beams 352, 354 may exit the reference module 350 in a collinear fashion. In FIG. 3A the first and second reference beams 352, 354 are shown side by side for purposes of illustration only.

In another embodiment, the detectors 302 and 304 can be configured to be photon detectors that will detect the integral signal. In yet another embodiment, these two detectors can also be used during operation to provide the servo feedback to control the reference phase. In this embodiment, for example, detector 302 will provide the inspection signal that has minimal pattern contrast, while detector 304 collects a signal that is generated with the reference beam 90 or 180 degrees out of phase from the inspection signal. For example, if, due to environment changes, the phase of the reference beam 352 changes, this change can be detected at the detector 302 and the direction of the change in phase can be determined using the change detected at the detector 304. Based on the detected change in phase of the reference beam 352, servo positioning of mirrors, such as the mirrors 372, 376, and 362 can be performed by detecting changes in the signals detected at the detectors 302 and 304.

Figure 4:
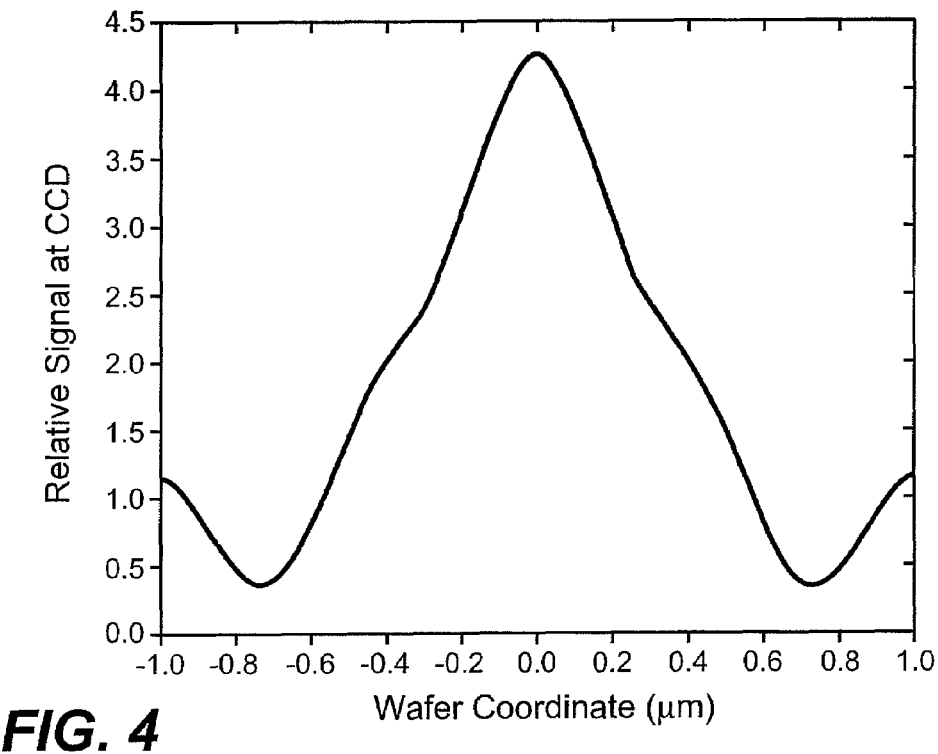
FIG. 4 is a plot of a simulated signal at a FIG. 3A detector for the sample of FIG. 1 as obtained using coherent detection techniques.

FIG. 4 is a plot of a simulated signal $I_{det(A)}$ at the detector 302 for the first interference pattern described above for the sample 100 shown in FIG. 1. In this plot, the amplitude of the first reference beam 352 is set to a higher value to boost the signal from the exposed portion 108 (FIG. 3A). A comparison of the plot of FIG. 4 with the plot of FIG. 2B illustrates that the signal at the exposed portion 108 is dramatically higher using the coherent method of optical inspection described above with reference to FIGS. 3A and 3B. Thus, the signal at the exposed portion 108 is more likely to be well above the noise floor of the associated detector, such as the detector 302.

Interference Contrast Enhancement

Figure 5:
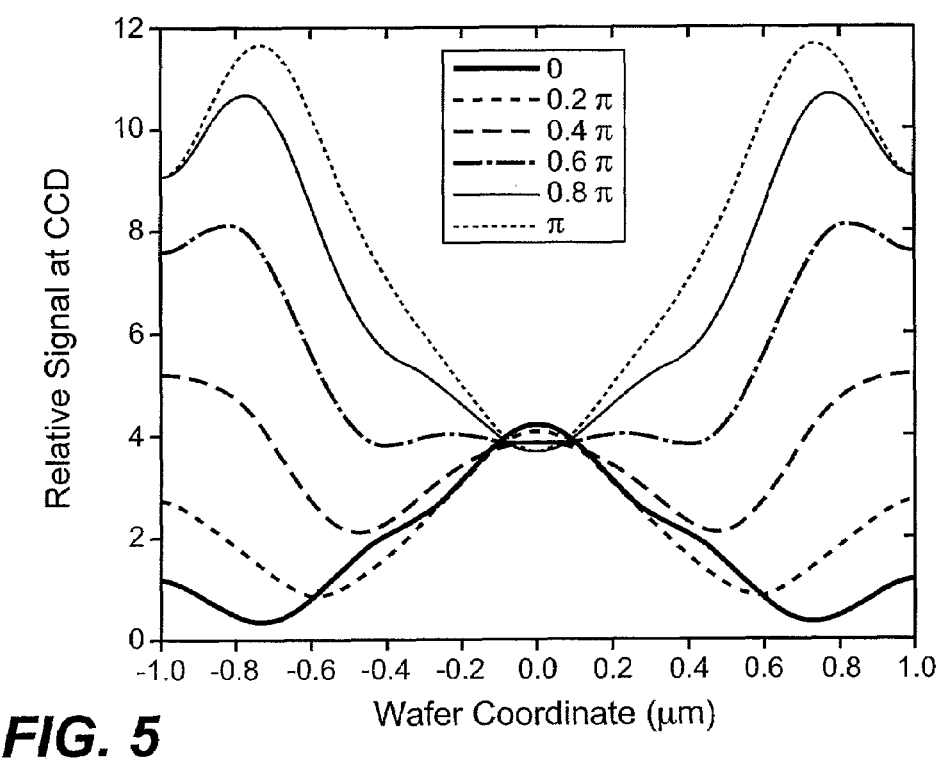
FIG. 5 is a plot of a simulated signal at a FIG. 3A detector for various phase difference conditions between a reference beam and a reflected beam.

FIG. 5 is a plot of a simulated signal at the detector 302 for various phase difference conditions between the first reference beam 352 and the reflected beam 328. As mentioned above, and as discussed in more detail below, adjusting the phase of the reference beam 352 to change the phase difference between the first reference beam 352 and the reflected beam 328 can enhance contrast of a first area, such as a defect area, of the first interference pattern relative to a second area of the first interference pattern. As shown in FIG. 5 different phase differences between the first reference beam 352 and the reflected beam 328 may produce significantly different signals at the detector 302.

FIGS. 6A, 6B, 6C, and 6D illustrate a simulated signal plot of array patterns obtained using the coherent detection methods described above with reference to FIGS. 3A and 3B. In each of the FIGS. 6A, 6B, 6C, and 6D a portion 602 of a sample is illustrated as having an array of contact holes 604 and therefore comprises a comparison or a reference pattern.

In FIGS. 6A and 6C, no film residue is disposed in any of the holes 604. In FIGS. 6B and 6D, hole 606 (at array index 3,5) has film residue (not shown) disposed therein. The film residue in this example creates a phase difference of a from the other contact holes 604. The contact holes 604 that do not have the film residue disposed therein exhibit a phase difference of $n*\pi+\pi/2$ relative to the background 608, where n comprises an integer. The contact holes 604 other than the hole 606 may be referred to as "nominal structures." As discussed below, the hole 606 in some of the FIGS. 6A, 6B, 6C, and 6D will exhibit little or no signal difference on detector 302 from the nominal structures (i.e., the other holes 604).

In the plots of FIGS. 6A and 6B, the phase of the first reference beam 352 is set to create high contrast between the background and the pattern of holes. Despite there being film residue in the hole 606, however, no significant signal difference is present between the plots of FIGS. 6A and 6B. Hence, in FIGS. 6A and 6B, there is low signal contrast in the defect area (i.e., at hole 606).

In FIGS. 6C and 6D, however, the phase of the reference beam is adjusted by a phase difference of $\pi$ from the background 608, which enhances the signal contrast at hole 606, but may decrease contrast between the background and the pattern of holes. As shown, in FIGS. 6C and 6D, the difference signal between the holes 604 and the background 608 is less than that of FIGS. 6A and 6B. Importantly, however, the signal difference in the area of the hole 606 in the plot of FIG. 6D is high and is easily detected by comparison with the plot of FIG. 6C.

The example of FIGS. 6A, 6B, 6C, and 6D illustrates the advantage of using a second reference beam that differs in phase from a first reference beam by π. As shown above in FIGS. 3A and 3B, the second reference beam 354 differs in phase from the first reference beam 352 by π. The second reference beam 354 interferes with the reflected beam 328 and generates a second interference pattern at the detector 304. Depending on the phase values of the various structures, or areas, of the sample being inspected, adjusting the phase of the reference beam may significantly improve contrast between a defect and the background pattern, between a defect structure and a nominal structure, or both.

In one embodiment, the phase of the reference beam is adjusted based on the first interference pattern detected at the detector 302 and the second interference pattern detected at the detector 304.

For array high aspect ratio inspection, in one embodiment, the phase for the reference beam may be adjusted so it results in minimal contrast for the array pattern. This setting would enhance the contrast between any anomaly and the background. The necessary phase setting for the reference beam can be determined based on the interference pattern detected at the detector 302 and the second interference pattern detected at the detector 304. For example, $$I_1 = I_B + I_R + 2\sqrt{I_B I_R} \cos(\phi_B - \phi_R) \approx 2I_R + 2I_R \cos(\phi_B - \phi_R)$$

$$I_2 = I_H + I_r + 2\sqrt{I_H I_R} \cos(\phi_H - \phi_R) \approx I_R$$

where $I_B$ is the intensity from the background,
$I_H$ is the intensity from the high aspect area and is typically significantly lower than $I_B$
$I_R$ is the intensity from the reference beam, and is typically set to be equal to $I_B$
$I_1$ is the resulting interference signal from the background, while $I_2$ is the one from the high aspect area.

In order to have minimal contrast for the array pattern, $I_1$ shall be similar to $I_2$. This condition can be met when the phase of the reference beam $\phi_R$ is set so $\cos(\phi_B - \phi_R) \sim -0.5$. To set this $\phi_R$ value, first we can acquire $I_1$ at any phase setting for the reference beam, $\phi_{R1}$, and also 180 degrees out of phase. These two data sets can be taken sequentially or taken simultaneously as outlined in FIG. 3A with detectors 302 and 304 during pre-scan. The optimal $\phi_R$ can be then determined from the data as follows.

$$I_1(R1) = 2I_R + 2I_R \cos(\phi_B - \phi_{R1})$$

$$I_1(R2) = 2I_R + 2I_R \cos(\phi_B - \phi_{R1} - \pi)$$

$$I_S \equiv I_1(R1) + I_1(R2) = 2I_R(2 + 2\cos(\phi_B - \phi_{R1} - \pi/2)\cos(\pi/2))$$

$$I_D \equiv I_1(R1) - I_1(R2) = 2I_R(2\sin(\phi_B - \phi_{R1} - \pi/2)\sin(-\pi/2))$$

$$I_D/I_S \cong -\sin(\phi_B - \phi_{R1} - \pi/2) \cong \cos(\phi_B - \phi_{R1})$$

The optimal reference phase can be set by adding an additional phase of $\cos^{-1}(I_D/I_S) + [(2n+1)\pi \pm \frac{1}{3}\pi]$ to the reference beam where n is an integer.

In another embodiment, the phase of the reference beam can be set to maximize the contrast between the defected area and the nominal pattern. For example, for two similar objects A, B where A represents the nominal pattern and B represents defect, the interference signals at the detector are $$I_A = I_0 + I_1 \cos(\phi_A - \phi_R)$$

$$I_B = I_0 + I_1 \cos(\phi_B - \phi_R)$$

$$\Delta I \equiv I_A - I_B = I_1 \left( 2\sin\frac{1}{2}(\phi_A + \phi_B - 2\phi_R)\sin\frac{1}{2}(\phi_B - \phi_A) \right)$$

For ΔI to be maximum, $$\frac{d(\Delta I)}{d\phi_R} \approx 0$$

Since $$\frac{d(\Delta I)}{d\phi_R} \cong 2I_1 \sin\frac{1}{2}(\phi_B - \phi_A)\cos\frac{1}{2}(\phi_A + \phi_B - 2\phi_R)(-1) \approx 0$$

$$\cos\frac{1}{2}(\phi_A + \phi_B - 2\phi_R)$$

shall be equal to $$\left(n + \frac{1}{2}\right)\pi,$$

where n is an integer

This means that when the reference phase is set to be $$\frac{\phi_A + \phi_B}{2} - \left(n + \frac{1}{2}\right)\pi,$$

the contrast between the interference signals from patterns A & B is maximal.

FIG. 7 is a plot of a difference signal across the area surrounding the hole 606 of FIG. 6D with the phase of the first reference beam 352 (FIG. 3) set at 0.0 and the phase of the second reference beam 354 set at π/2. In the plot of FIG. 7, the phase of the nominal contact hole 604 is at 0.4π, rather than at 0.5π as used above with reference to FIGS. 6A-6D. As shown in FIG. 7, the second reference beam 354 causes a significantly higher difference in the relative signal than the first reference beam 352, in this example.

Pattern Subtraction through Interference

As mentioned above, one challenge associated with inspection of a sample, such as a semiconductor wafer, is detecting film residue, or other matter, at a bottom portion of a high aspect ratio structure, such as a hole or trench. In some applications, the sample includes a repeating array of high aspect ratio structures in a pattern. One example of such a sample is the portion 602 of the sample shown in FIG. 6A, which includes a repeating array of contact holes 604.

For samples that include such a repeating pattern of structures, it may be desirable in some applications to remove, or suppress, the regular, nominal pattern from the analysis to enhance the defect area. According to one embodiment, differential interference is used to measure the difference between a defect pattern and a nominal pattern.

The interference may be accomplished, for example, using division by wavefront interference, such as by using Fourier filtering. The interference may also be accomplished by division by amplitude interference, such as by shearing through polarization or beam-splitting.

Figure 8:
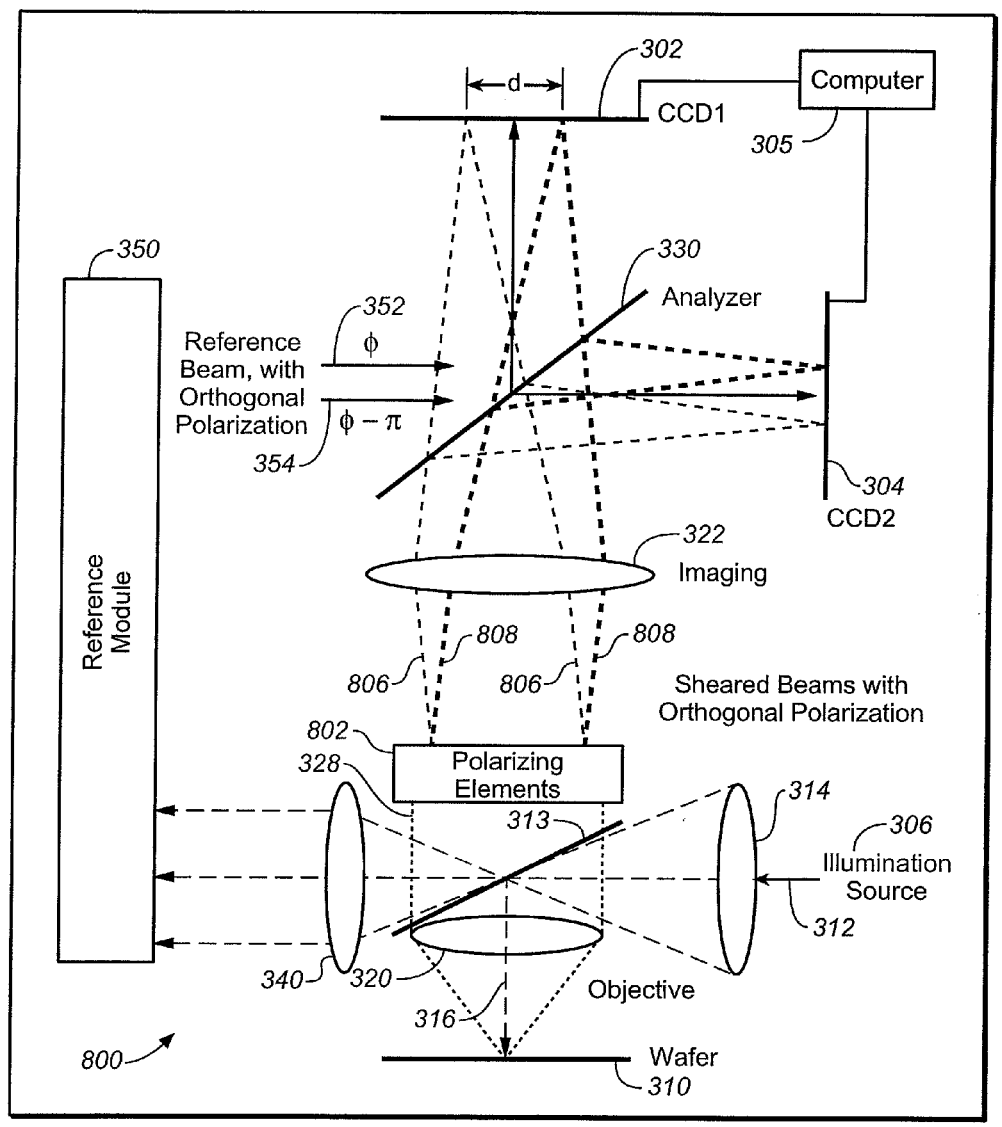
FIG. 8 schematically illustrates an example imaging system in accordance with another embodiment of the present invention.

FIG. 8 is a schematic view of an example inspection and imaging system 800 according to one embodiment of the present invention for inspecting the sample 310 having a repeating array of structures with adjacent structures being separated by a distance d as measured at the detector. In one embodiment, the sample 310 may comprise a semiconductor wafer having an array of contact holes. As shown in FIG. 8, imaging system 800 is identical to the imaging system 300 shown in FIG. 3A and described above, except as follows.

The imaging system 800 includes polarizing elements 802 positioned between the beam splitter 313 and the imaging lens 322. The polarizing elements 802 generally receive the reflected beam 328, separate the reflected beam 328 into first and second laterally separated beams 806, 808 and phase shift the second laterally separated beam 808 by π, or 180 degrees. The polarizing elements 802 laterally shift the beams 806, 808 such that they are laterally separated by a multiple of the distance d at the detector 302, where the distance d is the distance between adjacent structures as measured at the detector 302 of a repeating array of structures of the sample 310. The beams 806, 808 then interfere with each other at the detector 302 where the beams 806, 808 are laterally offset by the distance d. Optionally, the first reference beam 352 also interferes with the first and second laterally shifted beams at the detector 302.

FIG. 8 illustrates two detectors 302 and 304. In some embodiments, however, only a single detector is employed.

Details regarding some embodiments of the polarizing elements 802 that laterally separate a beam and introduce a phase shift into one of the laterally separated beams are well-known and are described in "Optical Interferometry" by M. Francon (ISBN 0122663500), the disclosure of which is hereby incorporated by reference. Additional details regarding one embodiment of the polarizing elements 802 are described below with reference to FIGS. 9, 10, 11A, and 11B.

Thus, the beam 806 is associated with a set of the repeating array of structures and the beam 808 is associated with the same set of the repeating array of structures. The beams are offset by a distance equal to a multiple of the distance d. Interfering the beams 806, 808 in this manner causes repeating structures in the pattern or image associated with the beam 808 to be subtracted from repeating structures in the pattern or image associated with the beam 806.

Figure 9A:
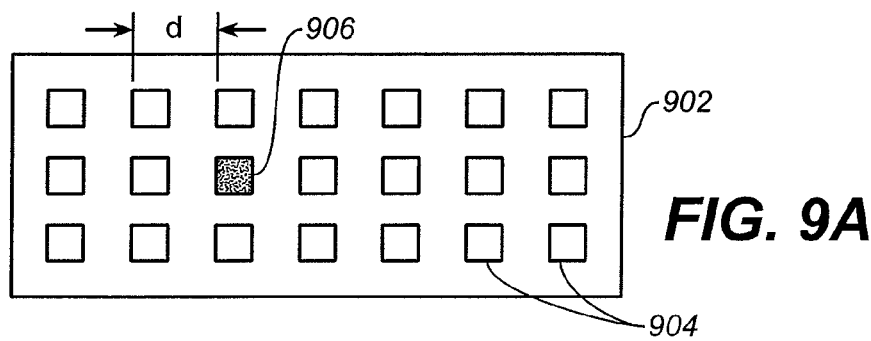
FIGS. 9A, 9B, and 9C illustrate lateral separation and subtraction aspects of pattern subtraction through differential interference techniques.
Figure 9B:
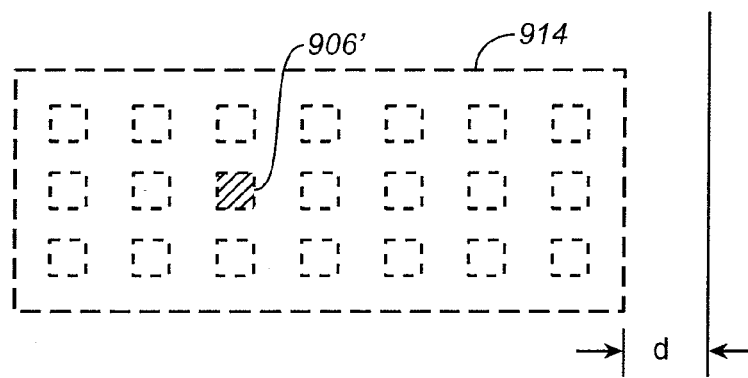
Figure 9C:
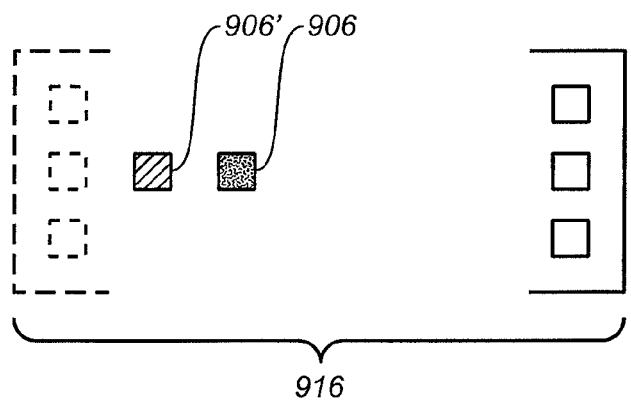

FIGS. 9A, 9B, and 9C illustrate lateral separation and subtraction aspects described above in accordance with one embodiment. As shown in FIG. 9A, a pattern 902 detected at detector 302 (FIG. 8) from a sample, such as the sample 310, includes an array of periodically repeating features 904, which are separated by a distance d, which is also the pitch of pattern 902. The sample 310 may comprise a portion of a semiconductor wafer and the each of the features 904 may comprise a contact hole formed in the semiconductor wafer 902. The features 904 may each alternatively comprise another HAR structure or a non-HAR structure. Feature 906 is a particular one of the features 904, located at position 2,3 and includes a defect.

Using the imaging system 800 described above, the illuminating beam 316 illuminates the sample 310 (FIG. 8) generating reflected beam 328. The reflected beam 328 enters the polarizing elements 802. The polarizing elements 802 then laterally separate the reflected beam 328 into beams 806, 808, such that the beam 808 is 180 degrees out of phase and laterally separated from the beam 806. The beams 806, 808 then pass through imaging lens 322 and are transmitted to at least one of the detectors 302, 304.

The beams 806, 808 interfere at at least one of the detectors 302, 304 such that they generate a first pattern 902 and a second pattern 914 (FIG. 9B) with periodically repeating features offset by distance d (shown in dashed lines). The first and second patterns 902 and 914 interfere with each other. The first pattern 902 shows the defect 906 and the second pattern 914 shows the defect 906'. The defect 906' is 180 degrees out of phase with the defect 906 and is laterally offset by the distance d. The first and second patterns 902 and 914 are laterally offset by the distance d at the detectors 302, 304 and are 180 degrees out of phase relative to each other, such that the first and second patterns 902, 914 destructively interfere to generate a difference pattern 916 (FIG. 9C). As shown, interfering the patterns 902 and 914 results in the subtraction of repeating background pattern and highlights the presence of the defect 906 in the difference pattern 916. The difference pattern 916 illustrates the defect 906 without the background comprising the pattern of features 904. By interfering the beams 806 and 808, the background pattern is substantially removed, thus permitting enhanced detection of the defect 906.

Figure 10:
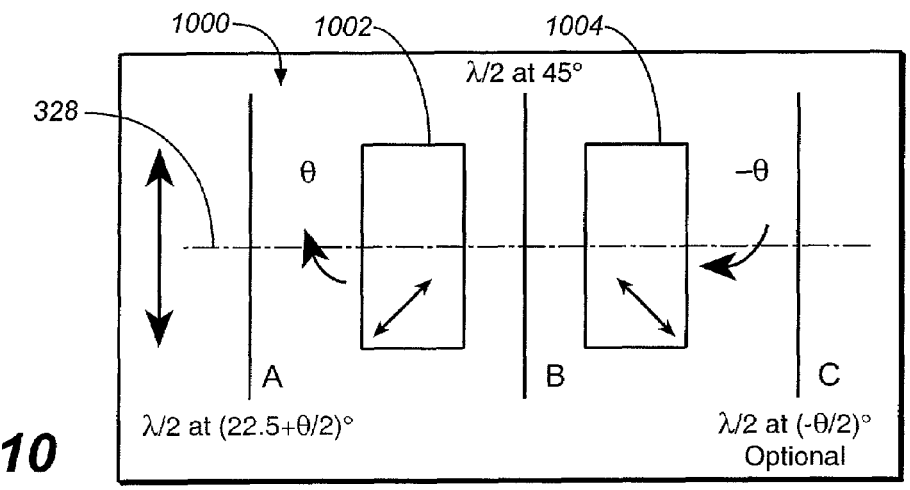
FIG. 10 illustrates an example mechanism for shearing a reflected beam according to an embodiment of the present invention.

FIG. 10 illustrates one embodiment of a mechanism 1000 for shearing the reflected beam 328 as performed by the polarizing elements 802 (FIG. 8). As shown, the mechanism 1000 includes a pair of Wollaston prisms 1002 and 1004, where θ is the separation angle of a prism and λ is the wavelength of the reflected beam 328.

In general, a Wollaston prism typically includes two wedges of quartz, calcite, or other suitable birefringent or doubly-refracting material, cut in such a way that their optical axes are oriented perpendicular when they are cemented together to form a prism. Light entering the Wollaston prism is split into two beams such that a phase difference between the two beams is created. Because the two beams are each derived from the same source prior to being sheared by the Wollaston prism, they are coherent and are capable of interference.

Referring back to FIG. 10, the prisms 1002 and 1004 are arranged such that the reflected beam 328 enters the prism 1002, is split into a pair of beams that have polarization vectors mutually perpendicular to each other. This pair of beams then pass through prism 1004. As the reflected beam 328 passes through the prism 1002, the prism 1002 shears, or separates, the beam into a pair of beams, with one of the beams being phase-shifted relative to the other beam. These beams then pass through prism 1004 where they are further displaced relative to each other.

Figure 11A:
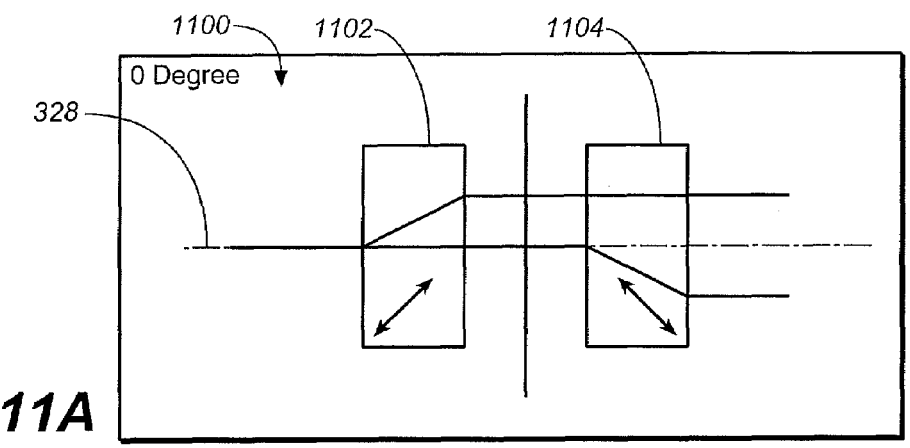
FIGS. 11A and 11B illustrate two orientations of the polarizing element implementation of FIG. 10.
Figure 11B:
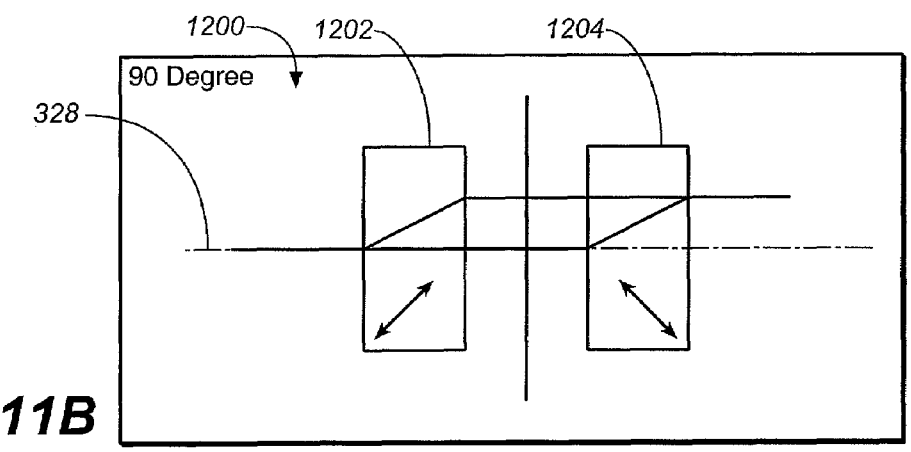

FIGS. 11A and 11B illustrate two orientations of the polarizing element implementation of FIG. 10. FIG. 11A shows a zero-degree configuration of a polarizing element 1100 that includes Wollaston prisms 1102 and 1104, which will shear, or separate, the reflected beam 328 to the maximum displacement of the sheared beams. The displacement depends on the angle separation of the Wollaston prism used. FIG. 11B shows a 90-degree configuration of a polarizing element 1200 that includes Wollaston prisms 1202 and 1204, which shear the reflected beam 328 to a minimum separation between the sheared beams. The amount of beam separation imposed by the Wollaston prisms may be adjusted between the zero-degree configuration of FIG. 11A and the 90-degree configuration of FIG. 11B to create beam shearing sufficient to provide an amount of beam separation appropriate for the pattern subtraction through interference described above.

Figure 12A:
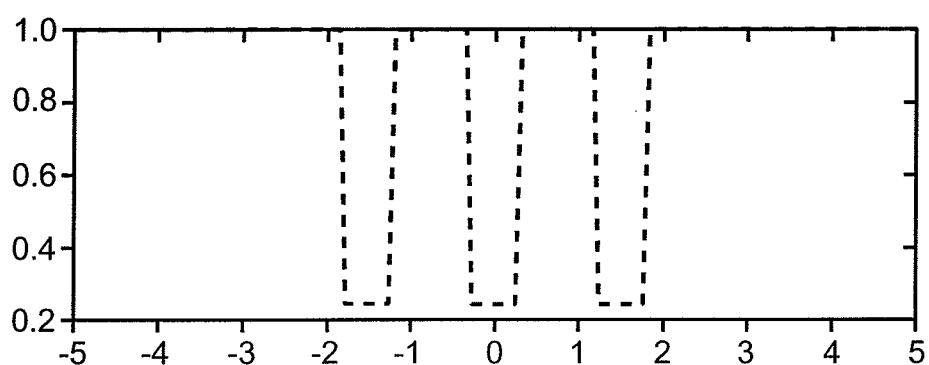
FIGS. 12A, 12B, 12C and 12D illustrate an example of pattern subtraction with amplitude division.
Figure 12B:
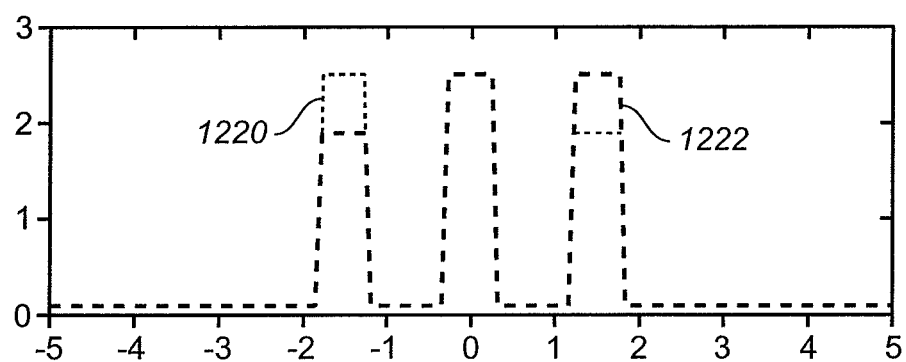

FIGS. 12A and 12B illustrate an example of pattern subtraction with amplitude division. In this example, a three-bar pattern that has a reflected amplitude ratio of 0.5 between the bottom of the structure and the top of the structure was simulated. FIG. 12A is the plot of the intensity profile of the simulated object. FIG. 12B shows the phase profile for two different patterns: one has a smaller phase at the right end of the bar and the other has a smaller phase at the left end instead. The inspection task is to compare these two structures and pickup the two phase differences at the two ends.

Figure 12C:
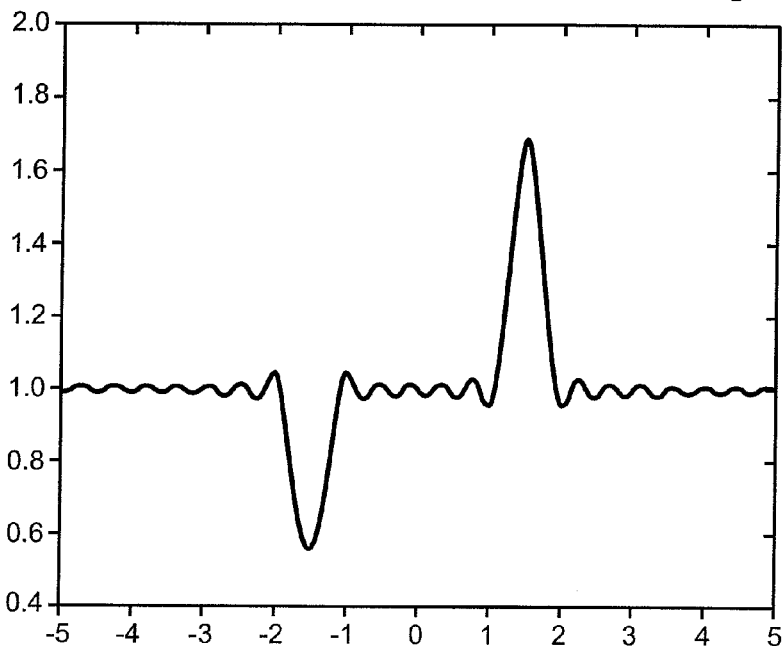
Figure 12D:
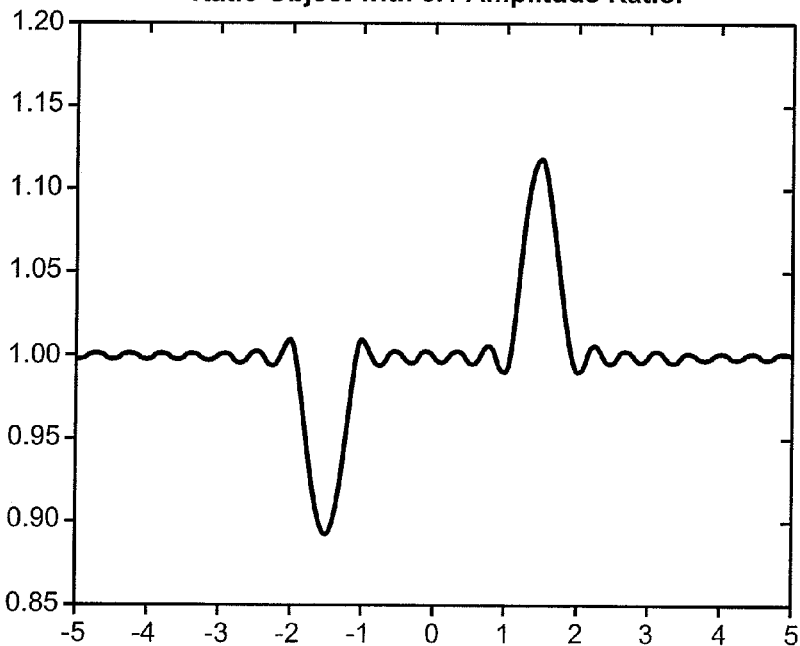

In this differential interference, the phase of the second pattern 1222 is shifted 180 degrees relative to the first pattern 1220, and this generates the subtraction effect between the two patterns. FIG. 12C illustrates the signal difference at the detector, such as detector 302 (FIG. 8) through differential interference detection of the object of FIG. 12A. FIG. 12D illustrates the signal difference for the object of FIG. 12A with a 0.1 amplitude ratio. Thus, by removing or suppressing the background pattern, significant signal contrast can be obtained. Further, FIGS. 12C and 12D demonstrate that with coherent detection, the impact from electronics noise may be reduced or minimized.

While various embodiments of the invention have been shown and described, it will be apparent to those skilled in the art that numerous alterations may be made without departing from the inventive concepts presented herein. Thus, the invention is not to be limited except in accordance with the following claims and their equivalents.

What is claimed is:

1. A method for inspecting a sample, the method comprising:
   illuminating a sample with an illumination beam to generate a reflected beam, the sample comprising an array of spaced features, with a distance d between adjacent features;
   laterally separating the reflected beam into first and second beams, the first and second beams being displaced from one another by a displacement distance equal to a multiple of the distance d, the second beam being about 180 degrees out of phase with the first beam;
   interfering the first beam and the second beam to generate an interference pattern; and
   detecting the interference pattern.

2. The method for inspecting a sample according to claim 1, wherein the interfering further comprises interfering a reference beam with the first and second beams to generate the interference pattern.

3. The method for inspecting a sample according to claim 1, wherein the interfering further comprises division amplitude interference.

4. The method for inspecting a sample according to claim 1 wherein the interfering further comprises division amplitude interference through polarization.

5. The method for inspecting a sample according to claim 1, wherein the interfering further comprises division wavefront interference through Fourier filtering.

6. The method for inspecting a sample according to claim 1, wherein the interfering further comprises division wavefront interference.

7. The method for inspecting a sample according to claim 1 wherein the interfering further comprises using a Nomarski layout.

8. The method for inspecting a sample according to claim 1, wherein the interfering the first beam and the second beam subtracts the second beam from the first beam to form the interference image.

9. The method for inspecting a sample according to claim 1, wherein the displacement distance equals the distance d.

10. The method for inspecting a sample according to claim 1, wherein the displacement distance equals twice the distance d.

11. An inspection apparatus for inspecting a sample having an array of features, each of the features being separated by certain distance from an adjacent feature, the inspection apparatus comprising:
    an illumination source for providing an illumination beam at the sample to generate a reflected beam;
    a polarizing element positioned to receive the reflected beam and configured to separate the reflected beam into first and second beams, the first and second beams being laterally separated and 180 degrees out of phase relative to each other; and
    a first detector aligned to detect a first interference pattern generated by interference of the first and second beams.

12. The inspection apparatus of claim 11, further comprising a reference module for generating a first reference beam, the first reference beam interfering with the first and second beams at the first detector.

13. The inspection apparatus of claim 11, wherein the polarizing element comprises at least one Wollaston prism.

14. The inspection apparatus of claim 11, further comprising:
    a reference module for generating first and second reference beams, the first reference beam interfering with the first and second beams at the first detector; and
    a second detector aligned to detect a second interference pattern generated by interference of the first beam, the second beam, and the second reference beam.

15. The inspection apparatus of claim 11, wherein the first interference pattern generated by interference of the first and second beams results from pattern subtraction of the first and second beams.

16. The inspection apparatus of claim 15, wherein the polarizing element comprises at least two Wollaston prisms, said at least two Wollaston prisms arranged to provide an amount of beam separation between the first and second beams appropriate for the pattern subtraction through interference at the first detector.

* * * * *